United States Patent [19]

Arneklev et al.

[11] 4,030,911
[45] June 21, 1977

[54] SULFIDE HERBICIDE ANTIDOTE COMPOSITIONS AND METHOD OF USE

[75] Inventors: Duane R. Arneklev, Plentywood, Mont.; Don R. Baker, Orinda, Calif.

[73] Assignee: Stauffer Chemical Company, Westport, Conn.

[22] Filed: June 27, 1975

[21] Appl. No.: 591,239

Related U.S. Application Data

[62] Division of Ser. No. 394,230, Sept. 4, 1973, abandoned.

[52] U.S. Cl. .................................... 71/98; 71/72; 71/76; 71/88; 71/93; 71/100; 71/110; 71/117; 71/118; 71/120; 260/326 S; 260/455 A; 260/465 D; 260/465 G; 260/558 S; 260/561 S; 260/583 EE; 260/609 R
[51] Int. Cl.$^2$ .......................................... A01N 9/12
[58] Field of Search ............. 71/98, 100, 77, 79; 47/57.6

[56] References Cited

UNITED STATES PATENTS

| | | | |
|---|---|---|---|
| 3,131,509 | 5/1964 | Hoffmann | 71/77 |
| 3,318,678 | 5/1967 | Thorup et al. | 71/95 |
| 3,555,160 | 1/1971 | Gier et al. | 71/98 |
| 3,564,768 | 2/1971 | Hoffmann | 47/57.6 |
| 3,702,759 | 11/1972 | Hoffmann | 71/77 |
| 3,719,466 | 3/1973 | Ahle | 47/57.6 |
| 3,871,865 | 3/1975 | Teach | 71/98 |

OTHER PUBLICATIONS

Van Rijn, "Chemical Weed Control in The Ord, etc.," (1964) CA62, p. 15358 (1965).
Meade et al., "Pre- and Postemergence Weed, etc.," (1959) CA54, p. 21606 (1960).

*Primary Examiner*—Glennon H. Hollrah
*Attorney, Agent, or Firm*—Harry A. Pacini

[57] ABSTRACT

Herbicidal compositions comprising an active herbicidal compound and an antidote therefor and the methods of use of the herbicide compositions are described herein; the antidote compound corresponds to substituted sulfides having the formula

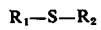

$$R_1 - S - R_2$$

wherein $R_1$ is selected from the group consisting of di-p-chlorophenylmethyl, phthalimidomethyl, pentachlorophenyl, alkenyl, haloalkyl, chloroalkenyl, aminoalkyl, hydroxyethyl, carboxymethyl, N-alkylcarbamoylmethyl, mono-chlorobenzamidoethyl, dichlorobenzamidoethyl, mono-bromobenzamidoethyl, β-S-ethylthiocarboxylaminoethyl and dichloroacetamidoethyl; and $R_2$ is selected from the group consisting of p-chlorophenyl, alkyl, haloalkyl, α-hydroxytrichloroethyl, alkenyl, chloroalkenyl, aminoalkyl, cyanoalkyl, cyanochloroalkyl, monochlorobenzamidoethyl, dichlorobenzamidoethyl, mono-bromobenzamidoethyl, β-S-ethylthiocarboxylaminoethyl and dichloroacetamidoethyl.

7 Claims, No Drawings

SULFIDE HERBICIDE ANTIDOTE COMPOSITIONS AND METHOD OF USE

This is a division, of application Ser. No. 394,230, filed Sept. 4, 1973 now abandoned.

BACKGROUND OF THE INVENTION

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in the U.S. Pat. Nos. 2,913,327, 3,037,853, 3,175,897, 3,185,720, 3,198,786 and 3,582,314. It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

DESCRIPTION OF THE INVENTION

It has been discovered that plants can be protected against injury by various herbicides of the thiocarbamate-type or substituted acetanilide-type, alone or mixed with other compounds and/or the tolerance of the plants can be substantially increased to the active compounds of the above-noted U.S. Patents by adding to the soil an antidote compound corresponding to the following formula:

$$R_1-S-R_2$$

wherein $R_1$ is selected from the group consisting of di-p-chlorophenylmethyl, phthalimidomethyl, pentachlorophenyl, alkenyl, chloroalkenyl, aminoalkyl, hydroxyethyl, carboxymethyl, N-alkylcarbamoylmethyl, haloalkyl, mono-chlorobenzamidoethyl, dichlorobenzamidoethyl, mono-bromobenzamidoethyl, β-S-ethylthiocarboxylaminoethyl and dichloroacetamidoethyl; and $R_2$ is selected from the group consisting of p-chlorophenyl, alkyl, haloalkyl, α-hydroxytrichloroethyl, alkenyl, chloroalkenyl, aminoalkyl, cyanoalkyl, cyanochloroalkyl, mono-chlorobenzylamidoethyl, dichlorobenzamidoethyl, mono-bromobenzamidoethyl, β-S-ethylthiocarboxylaminoethyl and dichloroacetamidoethyl.

In the above description, the following embodiments are intended for the various substituent groups: For $R_1$, alkenyl preferably includes those members containing at least one olefinic double bond and from 3 to 6 carbon atoms, inclusive, in both branched and straight chain configurations; chloroalkenyl includes mono-, di-, tri- and tetra-chlorosubstitution in alkenyl moieties having 3 to 6 carbon atoms, inclusive; the term aminoalkyl includes those members having at least one amino group ($NH_2-$) and an alkyl moiety having from 1 to 6 carbon atoms, inclusive. For $R_2$, alkyl preferably includes those members having from 1 to 8 carbon atoms, inclusive, in both branched and straight chain configurations; alkenyl preferably includes those members containing at least one olefinic double bond and from 3 to 6 carbon atoms, inclusive, in both branched and straight chain configurations; chloroalkenyl includes mono-, di-, tri- and tetra-chloro substitution in alkenyl moieties having 3 to 6 carbon atoms, inclusive; aminoalkyl includes those members having at least one amino group ($NH_2-$) and an alkyl moiety having from 1 to 6 carbon atoms, inclusive; cyanoalkyl includes those members having at least one cyano group ($-CN$) and an alkyl moiety having from 1 to 4 carbon atoms; cyanochloroalkyl includes those members having at least one cyano group, from 1 to 4 chlorine atoms, inclusive, and an alkyl moiety having from 2 to 6 carbon atoms, inclusive. The term haloalkyl preferably includes those alkyl members substituted with at least one halogen, selected from chlorine and bromine and having from 1 to 4 carbon atoms.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate or other herbicide with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, safening agent, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula can be prepared by several different procedures depending upon the starting materials.

GENERAL PROCEDURE FOR PREPARATION OF ALLYL AND BENZYL SULFIDES

The active halide (allyl or benzyl type) is dissolved in isopropyl alcohol or other suitable solvent, and sodium sulfide nona-hydrate which had been coarsely ground was added. The addition is at reduced temperature, approximately 15° C. At the end of the reaction, the precipitated sodium chloride is removed by filtration and the solvent removed in vacuo. The residue is taken up in benzene and ether and washed with three portions of water. The solution is dried and the solvent distilled in vacuo.

GENERAL PROCEDURE FOR PREPARATION OF MIXED SULFIDES

An organo mercaptan is dissolved in a suitable solvent, such as dioxane, isopropyl alcohol or the like. Sodium hydroxide solution is added and the reaction mixture heated. An active organo halide is added and the mixture refluxed. Work-up is by normal procedures of extraction, solvent removal, distillation or crystallization.

The compounds and the present invention and their preparation are more particularly illustrated by the following examples. Following the examples of preparation is a table of compounds which may be prepared according to the procedures described herein. Compound numbers have been assigned to them and are used for identification through the balance of the specification.

EXAMPLE I

Preparation of bis-(3,3-dichloroallyl)-sulfide 1,1,3-trichloropropene-1 (1100 g., 7.5 M) was dissolved in one liter of isopropanol and sodium sulfide nona-hydrate (900 g., 3.75 M) which had been coarsely powdered, was added at one time at 15° C. The mixture was stirred at 25°–30° C. for 3 hours and at 50° C. for 2 hours. It was allowed to stand overnight at room temperature. The precipitated sodium chloride was filtered off and the solvent removed in vacuo. The residual oil was taken up in a mixture of one liter of benzene and one liter of ether and washed with three 400 ml. portions of water. The solution was dried over magnesium sulfate and the solvent removed in vacuo. The residual solvent was removed at about 0.5 mm. There was obtained a red brown liquid, yield: 853 g. (90%). Structure was confirmed by NMR spectroscopy. The product distilled at b.p. 75°–77°/35mm.

EXAMPLE II

Preparation of bis-(β-m-chlorobenzamidoethyl)sulfide

To a solution of bis-(β-aminoethyl)sulfide (2.5 g., 0.021 M) and sodium hydroxide (1.6 g., 0.04 M) in 20 ml. of water and 40 ml. of ether was added a solution of m-chlorobenzoyl chloride (7.0 g., 0.04 M) in 15 ml. of ether at 10°–20° C. A precipitate appeared. The mixture was stirred 45 minutes at room temperature and the solid filtered, washed with water and dried. The product was a white solid. m.p. 150°–152° C. Its structure was confirmed by IR spectroscopy. Yield: 7.0 g. (88%).

TABLE I $R_1-S-R_2$

| COMPOUND NUMBER | $R_1$ | $R_2$ | m.p. ° C. or $N_D^{30}$ |
|---|---|---|---|
| 1 | (Cl-phenyl)$_2$CH | p-Cl-phenyl | 1.6460 |
| 2 | phthalimido-N-CH$_2$ | CH(CH$_3$)$_2$ | 57–62 |
| 3 | CH$_3$C(O)—NHCH$_2$CH(CH$_3$)$_2$ | p-Cl-phenyl | 107–112 |
| 4 | phthalimido-N-CH$_2$ | CH$_2$CH$_3$ | 64–72 |
| 5 | phthalimido-N-CH$_2$ | CH$_2$CH$_2$CH$_3$ | 1.5561 |
| 6 | pentachlorophenyl | CH$_2$CH$_2$Cl | 133–134 |
| 7 | p-Cl-phenyl | CHCl$_3$ with OH | 73–76 |
| 8 | CCl$_2$=CHCH$_2$ | CCl$_2$=CHCH$_2$ | 75–77/35 mm. |
| 9 | phenyl | CCl$_2$CH$_2$C≡N | 1.6073 |
| 10 | CCl$_2$=CClCH$_2$ | CH$_2$CH$_3$ | 1.5325 |

TABLE I-continued $R_1$—S—$R_2$

| Compound Number | $R_1$ | $R_2$ | m.p. °C. or $N_D^{30}$ |
|---|---|---|---|
| 11 | $CH_3CCl=CHCH_2$ | $CH_3CCl=CHCH_2$ | 1.5387 |
| 12 | $CH_2\overset{O}{\overset{\|}{C}}-OH$ | $CH_2C\equiv N$ | 1.5217 |
| 13 | $CHCl=CHCH_2$ | $CHCl=CHCH_2$ | 1.5270 |
| 14 | $CH_2CHCH_2$ | $CH_2=CHCH_2$ | 1.4850 |
| 15 | $HOCH_2CH_2$ | $CH_3CH_2$ | 1.4816 |
| 16 | $CCl_2=CClCH_2$ | $CCl_2=CClCH_2$ | 1.5810 |
| 17 | phenyl | $CH_2CH=CCl_2$ | 1.5905 |
| 18 | $ClCH_2CH_2CH_2$ | $CH_2CH_2CH_2Cl$ | 1.4528 |
| 19 | $HOCH_2CH_2$ | $n\text{-}C_8H_{17}$ | 1.4710 |
| 20 | $H_2N-CH_2CH_2$ | $CH_2CH_2NH_2$ | b.p. 64–67° C. .3–.4mm |
| 21 | $C_2H_5S\overset{O}{\overset{\|}{C}}NHCH_2CH_2$ | $CH_2CH_2NH\overset{O}{\overset{\|}{C}}SC_2H_5$ | 130–132 |
| 22 | 2,4-dichlorophenyl-C(=O)-NHCH$_2$CH$_2$ | CH$_2$CH$_2$NHC(=O)-2,4-dichlorophenyl | 148–151 |
| 23 | 3-chlorophenyl-C(=O)-NHCH$_2$CH$_2$ | CH$_2$CH$_2$NHC(=O)-3-chlorophenyl | 150–152 |
| 24 | 3-bromophenyl-C(=O)-NHCH$_2$CH$_2$ | CH$_2$CH$_2$NHC(=O)-3-bromophenyl | 170–172 |
| 25 | $Cl-CH=CCl-CH_2$ | $CH_2CCl=CHCl$ | red/brown liquid |
| 26 | $Cl_2CH\overset{O}{\overset{\|}{C}}NHCH_2CH_2$ | $CH_2CH_2NH\overset{O}{\overset{\|}{C}}CHCl_2$ | 111–115 |

The compounds of this invention were employed in effective herbicidal antidote compositions comprising thiocarbamates or substituted acetanilides in combination with antidote compounds described hereinabove. They were tested in the following manner.

CORN SEED TREATMENT TEST

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six DeKalb XL 374 field corn seeds were planted in each row. Rows were approximately 1½ inches apart in the flat. Seeds were treated by placing 50 mg. of the antidote compound with 10 grams of corn seed in a suitable container and shaking them until the seeds were uniformly covered with the compound. Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had been removed just prior to planting. Flats were placed on greenhouse benches where temperatures ranged from 70°–90° F. Flats were watered by sprinkling as needed to assure good plant growth. Percent control ratings were taken two to three weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests are tabulated in Table II.

D. 6 lb/A: 4312 mg. of ORDRAM 6E (71.3% a.i.) was diluted with 500 ml. of deionized water so that 4 ml. of the stock solution equaled 6 lb/A when applied to a flat.

Antidote stock solutions are prepared by diluting 102 mg. of technical material with 10 ml. of acetone 1% Tween 20 (polyoxyethylene sorbitan monolaurate) so that 2 ml. equals 5 lb/A flat.

After the soil is treated with both herbicide and additive, the soil is transferred from the mixer back into the flat where it is then prepared for seeding. The initial step in preparation is to remove a one pint sample of soil from each flat to be retained and used to cover the seeds after planting. The soil is then leveled and rows one-quarter inch deep are made in each flat. Flats treated with the herbicide and additive are seeded with corn (Zea maize), sugarbeets (Beta vulgare), sunflower

TABLE II

| | Per Cent Injury to Corn from EPTC* | | |
|---|---|---|---|
| | | Seed Treatment Test | |
| | | Per Cent Injury, weeks | |
| COMPOUND NUMBER | EPTC lb/A | Treated Seed (0.5% w/w) (2 wks) | Untreated Seed Adjacent Row (3 wks) |
| 1 | 6 | 50 | 50 |
| 2 | 6 | 40 | 65 |
| 3 | 6 | 50 | 80 |
| 4 | 6 | 65 | 70 |
| 5 | 6 | 80 | 70 |
| EPTC Untreated Seed | — | 90 | — |

*= S-ethyl dipropylthiocarbamate

PROCEDURE: MULTICROP ANTIDOTE SCREEN

Flats were filled with Felton loamy sand soil. A variety of grass and broadleaf crops were used in these tests. EPTAM (EPTC) was incorporated at ½, 3 or 5 lb/A, while a constant rate of 5 lb/A of the additive was used. LASSO (EPTC) or ORDRAM (S-ethyl hexahydro-1-H-azepine-1-carbothioate) and the candidate herbicide antidote were applied separately by pipetting measured amounts of the appropriate stock solutions into the soil during incorporation in a 5 gallon rotary cement mixer. Stock solutions were prepared as follows:

A. ½ lb/A: 670 mg. of EPTC 6E (75.5% a.i.) is diluted with 500 ml. of deionized water so that 2 ml. equals ½ lb/A flat.

B. 5 lb/A: 6700 mg. of EPTC 6E (75.5% a.i.) is diluted with 500 ml. of deionized water so that 2 ml. equals 5 lb/A flat.

C. 2 lb/A: 427 mg. LASSO 4E is diluted with 100 ml. of deionized water so that 1 ml. equals 2.05 mg. (a.i.) and 4 ml. equals 8.2 mg. equivalent to 2 lb/A flat.

(Helianthus annus), cotton (Gossypium hirsutum), soybeans (Glycine max) and oilseed rape (Brassica napus). Flats treated with ½ lb/A of EPTAM are seeded with red oats (Avena byxantina), milo (Sorghum vulgare), wheat (Triticum aestivum), giant foxtail (Seteria feberii), rice (Oryza sativa) and barley (Hordeum vulgare). Flats treated with 2 lb/A of LASSO are seeded with corn (Zea maize), wheat (Triticum aestivum), rice (Oryza sativa), milo (Sorghum vulgare), and barley (Hordeum vulgare). Seeds are then covered with the pint soil sample removed prior to seeding.

The flats are then placed on greenhouse benches where temperatures are maintained between 70°–90° F. The soil is watered by sprinkling to assure good plant growth.

Injury ratings are taken at 2, 3 or 4 weeks after the treatments are applied. Soil treated with the herbicides alone at ½, 2, 3, 5 or 6 lb/A is included to provide a basis for determining the amount of injury reduction provided by the herbicide antidotes. The percent protection is determined by a comparison with flats not treated with the candidate antidote, but with the herbicide alone. Results are given in Table III.

TABLE III

| | MULTICROP SCREEN RESULTS | | | |
|---|---|---|---|---|
| | PER CENT PROTECTION | | | |
| COMPOUND NUMBER | | Rate of Herbicide lb/A | Rate of Antidote lb/A | Crop | % Protection (4 wks) |
| 6 | EPTC[a] | 3.0 | 5.0 | corn | 100 |
| | EPTC | 3.0 | 5.0 | soybeans | 40 |
| 7 | EPTC | 3.0 | 5.0 | corn | 75 |
| 8 | EPTC | 0.5 | 5.0 | sorghum | 100 |
| | EPTC | 0.5 | 5.0 | rice | 30 |
| | EPTC | 3.0 | 5.0 | corn | 100 |
| | ORDRAM[b] | 6.0 | 5.0 | rice | 72 |
| | LASSO[c] | 2.0 | 5.0 | wheat | 38 |
| | LASSO | 2.0 | 5.0 | sorghum | 100 |
| 9 | EPTC | 0.5 | 5.0 | sorghum | 50 |

TABLE III-continued

MULTICROP SCREEN RESULTS
PER CENT PROTECTION

| COMPOUND NUMBER | | Rate of Herbicide lb/A | Rate of Antidote lb/A | Crop | % Protection (4 wks) |
|---|---|---|---|---|---|
| | EPTC | 0.5 | 5.0 | rice | 44 |
| 10 | EPTC | 3.0 | 5.0 | mustard | 100 |
| 11 | EPTC | 0.5 | 5.0 | sorghum | 50 |
| | EPTC | 0.5 | 5.0 | rice | 38 |
| | EPTC | 3.0 | 5.0 | corn | 67 |
| 12 | EPTC | 3.0 | 5.0 | corn | 100 |
| 13 | EPTC | 5.0 | 5.0 | sunflower | 67 (3) |
| 14 | EPTC | 0.5 | 5.0 | rice | 100 (3) |
| | ORDRAM | 6.0 | 5.0 | rice | 30 |
| 15 | EPTC | 0.5 | 5.0 | rice | 100 (3) |
| 16 | EPTC | 0.5 | 1.0 | rice | 11 |
| 17 | EPTC | 0.5 | 5.0 | sorghum | 67 |
| | EPTC | 3.0 | 5.0 | corn | 83 |
| 18 | EPTC | 0.5 | 5.0 | barley | 45 |
| 19 | EPTC | 5.0 | 5.0 | sunflower | 67 |
| 20 | EPTC | 5.0 | 5.0 | rape | 87 |
| 21 | EPTC | 0.5 | 5.0 | rice | 86 |
| 22 | EPTC | 0.5 | 5.0 | rice | 100 |
| | EPTC | 5.0 | 5.0 | sunflower | 75 |
| 23 | EPTC | 0.5 | 5.0 | rice | 100 |
| | EPTC | 5.0 | 5.0 | sunflower | 75 |
| 24 | EPTC | 0.5 | 5.0 | rice | 62 |
| 25 | EPTC | 5.0 | 5.0 | corn | 15 |
| 26 | EPTC | 5.0 | 5.0 | corn | 45 |

*a*= S-ethyl dipropylthiocarbamate
*b*= S-ethyl hexahydro-1H-azepine-1-carbothioate
*c*= 2-chloro-2',6'-diethyl-N-(methoxymethyl)acetamilide The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.01 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The rates are within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compounds to the area or plant locus where control is desired. The compositions as set forth in this invention include those wherein the preferred active herbicidal compound is selected from ETC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, 2-chloro-2',6'-diethyl-N-(methoxymethyl)acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-s-triazine, 2(4-chloro-6-ethylamine-s-triazine-2-yl-amino)-2-methylpropionitrile, 2-chloro-4-cyclopropylamino-6-isopropylamino-s-triazine, 2,4-dichlorophenoxyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

What is claimed is:

1. The method of protecting a crop from injury due to a thiocarbamate herbicide, comprising applying to the habitat prior to planting from about 0.01 to about 15 parts by weight for each part by weight of the thiocarbamate herbicide an antidote compound corresponding to the formula $$R_1-S-R_2$$

wherein $R_1$ is selected from the group consisting of, chloroalkyl, having from 1 to 4 carbon atoms, inclusive, hydroxyethyl, carboxymethyl, β-S-ethylthiocarboxylaminoethyl and dichloroacetamidoethyl; and $R_2$ is selected from the group consisting of alkyl, having from 1 to 8 carbon atoms, inclusive, chloroalkyl, having from 1 to 4 carbon atoms, inclusive, cyanoalkyl, having at least one cyano group and an alkyl moiety having from 1 to 4 carbon atoms, inclusive, β-S-ethylthiocarboxylaminoethyl and dichloroacetamidoethyl.

2. The method according to claim 1 in which $R_1$ is dichloroacetamidoethyl and $R_2$ is dichloroacetamidoethyl.

3. The method according to claim 1 in which $R_1$ is chloroalkyl, and $R_2$ is, chloroalkyl.

4. The method according to claim 3 in which $R_1$ is 3-chloropropyl and $R_2$ is 3-chloropropyl.

5. The method according to claim 1 in which $R_1$ is β-S-ethylthiocarboxylaminoethyl and $R_2$ is β-S-ethylthiocarboxylaminoethyl.

6. The method according to claim 1 in which $R_1$ is carboxymethylene and $R_2$ is cyanomethylene.

7. The method according to claim 1 in which $R_1$ is hydroxyethyl and $R_2$ is ethyl.